United States Patent
Jiang et al.

(10) Patent No.: US 6,670,191 B2
(45) Date of Patent: Dec. 30, 2003

(54) METHOD FOR QUANTITATIVELY ANALYZING FRAGMENTED RED BLOOD CELLS

(75) Inventors: Meiyi Jiang, Kobe (JP); Hideaki Matsumoto, Takasago (JP); Shion Imoto, Kobe (JP); Katsuyasu Saigo, Kobe (JP); Shunichi Kumagai, Amagasaki (JP)

(73) Assignee: Sysmex Corporation, Hyogo (JP)

( * ) Notice: Subject to any disclaimer, the term of this patent is extended or adjusted under 35 U.S.C. 154(b) by 262 days.

(21) Appl. No.: 09/801,642

(22) Filed: Mar. 9, 2001

(65) Prior Publication Data
US 2001/0053551 A1 Dec. 20, 2001

(30) Foreign Application Priority Data
Jun. 20, 2000 (JP) ........................ 2000-184853

(51) Int. Cl.$^7$ .............................................. G01N 33/48
(52) U.S. Cl. ........................... 436/63; 436/10; 436/164; 436/172; 422/73; 422/82.05; 422/82.08; 356/39; 356/337
(58) Field of Search .............. 436/63, 8, 10, 436/164, 172, 174, 800; 422/73, 82.05, 82.08; 356/39, 336, 337

(56) References Cited

U.S. PATENT DOCUMENTS

| | | | | |
|---|---|---|---|---|
| 5,298,426 A | * | 3/1994 | Inami et al. | 436/63 |
| 5,858,667 A | * | 1/1999 | Dertinger et al. | 435/6 |
| 6,118,522 A | * | 9/2000 | Kanai et al. | 356/73 |
| 6,133,995 A | * | 10/2000 | Kubota | 356/73 |
| 6,525,807 B1 | * | 2/2003 | Morikawa et al. | 356/72 |

FOREIGN PATENT DOCUMENTS

JP    B22674704    7/1997

OTHER PUBLICATIONS

ZR Zeigler, et al. "Bone marrow transplant–associated thrombotic microangiopath: a case series" Bone Marrow Transplatation, 15, pp. 247–253 (1995).
J. David Bessman, M.D. "Red Blood Cell Fragmentation" American Journal of Clinical Pathology, 90, p. 268–273 (1988).

* cited by examiner

Primary Examiner—Maureen M. Wallenhorst
(74) Attorney, Agent, or Firm—Birch, Stewart, Kolasch & Birch, LLP (57) ABSTRACT

A method for quantitatively analyzing fragmented red blood cells includes the steps of: preparing a two-dimensional particle distribution diagram on the basis of a scattered light intensity and fluorescent light intensity; establishing a red blood cell distribution area on the distribution diagram, and counting particles falling within the red blood cell distribution area for determination of the total number A of red blood cells; establishing a fragmented red blood cell distribution area in a region in which the scattered light intensity and the fluorescent light intensity are low within the red blood cell distribution area, and counting particles falling within the fragmented red blood cell distribution area for determination of the number B of fragmented red blood cells; and calculating a value B/A, and calculating a content by percentage F of the fragmented red blood cells from a conversion function $F=f(B/A)$.

8 Claims, 8 Drawing Sheets

METHOD FOR QUANTITATIVELY ANALYZING FRAGMENTED RED BLOOD CELLS

CROSS-REFERENCE TO RELATED APPLICATION

This application is related to Japanese Patent Application No. 2000-184853 filed on Jun. 20, 2000, whose priority is claimed under 35 USC §119, the disclosure of which is incorporated by reference in its entirety.

BACKGROUND OF THE INVENTION

1. Field of the Invention

The present invention relates to a method for quantitatively analyzing fragmented red blood cells (FRCs) and, particularly, to a method for quantitatively analyzing fragmented red blood cells observed in peripheral blood in the case of various diseases such as cardiovascular abnormality, congenital or acquired hemolytic anemia, disseminated intravascular coagulation, hemolytic uremic syndrome and TTP (Thrombotic Thrombocytopenic Purpura).

2. Description of the Related Art

With recent studies on BMT-TMA (bone marrow transplantation-associated thrombotic microangiopathy), attention has been given to FRC % (the percentage of fragmented red blood cells) in peripheral blood, which is regarded as an important index for early diagnosis of BMT-TMA. A BMT-TMA grading system (grades of 0 to 4) was developed on the basis of the FRC % as well as the lactate dehydrogenase (LDH) (Bone Marrow Transplantation, 15, p. 247–253, 1995). The grades are defined as follows:

Grade 0 Normal LDH and FRC$\leq$1.2%
Grade 1 Normal LDH and FRC$\geq$1.3%;
Grade 2 Increased LDH and FRC=1.3% to 4.8%;
Grade 3 Increased LDH and ERG=4.9% to 9.6%; and
Grade 4 Increased LDH and ERG$\geq$9.7%

The FRC % can be determined through visual observation of a peripheral blood smear film. In general, the FRCs are not quantitatively analyzed, but analyzed for detection thereof. Although there are several reports which state that evidence of FRCs can be detected on the basis of a red blood cell size distribution standardized for automatic red blood cell counters (American Journal of Clinical Pathology, 90, p. 268–273, 1988), the quantitative analysis of the ERCs still relies on the visual observation of a smear film, and the results of the observation may vary significantly with different observers due to absence of criteria to be referenced.

SUMMARY OF THE INVENTION

In view of the foregoing, the present invention is directed to a method for quantitatively analyzing fragmented red blood cells, which can determine the FRC % with a high level of accuracy by establishing a specific area on a scattergram of a flow cytometer.

According to the present invention, there is provided a method for quantitatively analyzing fragmented red blood cells, comprising the steps of: adding a nucleic acid staining fluorochrome dye to a blood sample for preparation of a specimen containing particles; allowing the specimen to flow through a flow cytometer, and measuring a scattered light intensity and a fluorescent light intensity for each particle in the specimen; preparing a two-dimensional particle distribution diagram on the basis of the measured scattered light intensity and fluorescent light intensity; establishing a red blood cell distribution area on the two-dimensional distribution diagram, and counting particles falling within the red blood cell distribution area for determination of the total number A of red blood cells; establishing a fragmented red blood cell distribution area in a region in which the scattered light intensity and the fluorescent light intensity are low within the red blood cell distribution area, and counting particles falling within the fragmented red blood cell distribution area for determination of the number B of fragmented red blood cells; and calculating a value B/A, and calculating a content by percentage F of the fragmented red blood cells from a conversion function F=f(B/A).

DETAILED DESCRIPTION OF THE INVENTION

The amount of a blood sample required for the method according to the present invention is about 10 $\mu$L to about 100 $\mu$L. A nucleic acid staining fluorochrome dye is added to the blood sample for preparation of a specimen, so that stained RNA (ribonucleic acid) in red blood cells can be detected by fluorescent light.

Examples of the nucleic acid staining fluorochrome dye include auramine O, acridine orange, thiazole orange, thioflavin T, pyronine Y, coriphosphine O, 3,3'-dimethylcarbocyanine iodide, oxazine 750, and polymethine fluorochrome dyes.

For the preparation of the specimen, a commercially available reticulocyte analytic reagent containing any of the aforesaid dyes and the blood sample are mixed in a ratio of 100:1 to 1000:1, and allowed to react with each other. At this time, a reaction temperature is preferably about 25° C. to about 50° C., more preferably 35° C. to 45° C. A reaction time may slightly vary depending on the dye contained in the reagent, but is preferably about 10 seconds to about 5 minutes, more preferably about 20 seconds to about 2 minutes, further more preferably about 20 seconds to about 60 seconds.

A flow cytometer to be employed in the present invention is adapted to pass a particle-containing liquid sample through a sheath flow cell, irradiate serially flowing particles with light, and detect a scattered light and a fluorescent light from each of the particles. For example, an automatic reticulocyte analyzer R-3500 available from Sysmex Corporation can be used as the flow cytometer.

A two-dimensional distribution diagram to be employed in the present invention is a scattergram which is prepared by plotting dots in a coordinate plane having two axes on the basis of coordinates representative of intensities of the scattered light and the fluorescent light from blood cells (particles). In this case, each plotted dot corresponds to each blood cell (particle).

The scattered light intensity and the fluorescent light intensity for each of the blood cells indicate a blood cell size and a ribonucleic acid (RNA) content, respectively, and are useful for discrimination of platelets, mature erythrocytes and reticulocytes on the two-dimensional distribution diagram. Fragmented red blood cells (FRCs), which each have a smaller size than the normal red blood cells and a lower RNA content than the platelets, can be detected on the two-dimensional distribution diagram (scattergram).

In the present invention, a red blood cell distribution area (gate G1) is established on the two-dimensional distribution diagram, and particles falling within this area are counted for determination of the total number A of red blood cells. A fragmented red blood cell distribution area (gate G2) is established in a region in which the particle size is smaller and the RNA content is lower (or the scattered light intensity and the fluorescent light intensity are lower) within the red blood cell distribution area, and particles falling within this area are counted for determination of the number B of fragmented red blood cells. Then, a value B/A is calculated, and the percentage F of fragmented red blood cells (FRC %) is calculated from a conversion equation $F=f(B/A)$, wherein f is a conversion factor. An equation indicative of a correlation between the value B/A and an FRC % determined through the visual observation method may be employed as the conversion equation $F=f(B/A)$. Further, a microerythrocyte distribution area (gate G3) is established in a region in which the particle size is greater than in the fragmented red blood cell distribution area (or the scattered light intensity is higher) within the red blood cell distribution area, and particles falling within this area are counted for determination of the number C of microerythrocytes. Thus, the percentage F of the fragmented red blood cells is calculated from the equation $F=f(B/A)$, and then corrected on the basis of a value C/A.

Where a greater amount of microerythrocytes are present in the blood sample, e.g., in the case of an asiderotic anemia patient, the microerythrocytes also fall within the gate G2 and are counted as the FRCs, so that the value F is greater than a true value. Therefore, the gate G3 is established for correction of the value F on the basis of the value C/A.

The establishment of the red blood cell distribution area (gate G1) is achieved by a known method such as disclosed in Japanese Patent No. 2674704.

In the step of calculating the fragmented red blood cell percentage FRC % in the present invention, the value F may be corrected on the basis of the value C/A when the value C/A is greater than a predetermined value α.

In the present invention, the value F may be calculated from an equation $F=f(B/A)C/A$ when the value C/A is not greater than the predetermined value α, and calculated on the basis of an equation $f=(B/A)\cdot\exp\{-a(C/A)\}$ (wherein a is a constant) when the value C/A is greater than the predetermined value.

The constant a is, for example, between about 0.4 and about 0.5, preferably a=0.43.

The predetermined value α is between 1 and 3 (%).

The conversion equation $F=f(B/A)$ can be expressed as a linear equation $F=m(B/A)+n$ wherein "_m_" and "_n_" are constants.

Embodiment

With reference to the attached drawings, the present invention will hereinafter be described in detail by way of an embodiment. It should be understood that the invention be not limited to the embodiment.

1. Flow Cytometer

Figure 1:
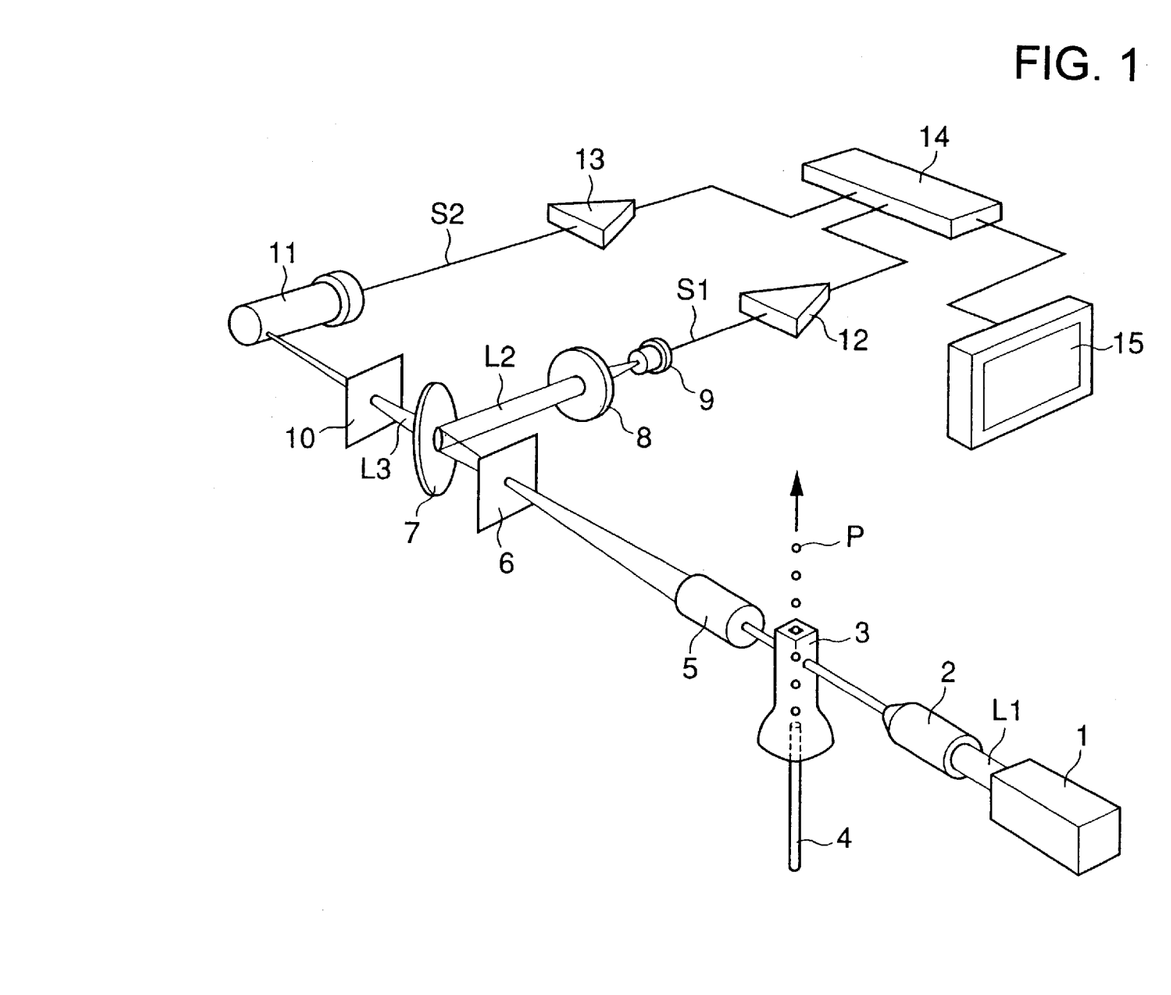
FIG. 1 is a diagram illustrating the construction of an automatic reticulocyte analyzer to be employed in an embodiment of the present invention.

FIG. 1 is a diagram illustrating the basic construction of an automatic reticulocyte analyzer (R-3500 available from Sysmex Corporation) to be employed as a flow cytometer in the embodiment of the present invention.

Referring to FIG. 1, a laser beam L1 of a wavelength of 488 nm emitted from an argon laser source 1 is focused on a sheath flow cell 3 by an irradiation lens system 2. A liquid sample containing particles (blood cells) is supplied into the sheath flow cell 3 from a sample nozzle 4. The particles serially flow in line in a sheath liquid stream not shown, and forward scattered light rays and forward fluorescent light rays from the particles (blood cells) P reach a dichroic mirror 7 via a collector lens 5 and a pinhole of a pinhole plate 6. The light rays are separated into forward scattered light L2 of a wavelength of 488 nm and forward fluorescent light L3 of a wavelength of 520 nm to 530 nm by the dichroic mirror 7.

The forward scattered light L2 is focused on a photodiode 9 by a condenser lens 8 thereby to be converted into an electric signal S1 indicative of the intensity of the forward scattered light. The forward fluorescent light L3, after being freed of stray light by a filter 10, is converted into an electric signal S2 indicative of the intensity of the fluorescent light. The signals S1 and S2 are respectively amplified by amplifiers 12 and 13, and then inputted to a data processor 14. The data processor 14 is adapted to display processing results on a display 15.

The data processor 14 prepares a two-dimensional distribution diagram (scattergram) on the basis of the signals S1, S2 by employing the forward fluorescent light intensity and the forward scattered light intensity as parameters, and displays the two-dimensional distribution diagram on the display 15. Further, the data processor 14 counts dots (particles) falling within an area established on the two-dimensional distribution diagram, and performs a predetermined computation. Then, the data processor 14 displays the counting result and the computation result on the display 15. The establishment of the area on the two-dimensional distribution diagram and the installation of a computation program are achieved by using input devices such as a keyboard and a disk drive (not shown).

The liquid sample to be supplied into the sample nozzle 4 of the analyzer shown in FIG. 1 is prepared in the following manner.

(1) A 10 μL blood sample is dispensed.
(2) The dispensed blood sample is diluted with 1950 μL of a diluent.
(3) The diluted sample is incubated at 35° C. for 25 seconds, while a 40 μL stain solution is added thereto with stirring.

About 2.8 μL of the incubated sample is dispensed and fed into the sheath flow cell 3 via the sample nozzle 4.

In this embodiment, a RETSEARCH™ diluent (containing a tris buffer of pH 8.25 and sodium propionate) and a RETSEARCH™ stain solution (an ethylene glycol solution containing 29.5 g/L of auramine O) available from Sysmex Corporation are used as the diluent and the stain solution, respectively.

2. Development of Analysis Method
(1) Establishment of FRC Detection Area with Model Samples (Containing Red Blood Cells Intendedly Fragmented)

A blood sample obtained from a healthy male donor was subjected to centrifugation at 1500 rpm for separation of red blood cells from white blood cells and platelets, and then the red blood cells thus obtained were washed three times in PBS (phosphate buffer saline) for preparation of a red blood cell sample. A portion (sample A) of the red blood cell sample was incubated at 50° C. for 100 seconds to induce fragmentation of red blood cells contained therein. Fragmented red blood cells (FRCs) thus obtained were confirmed through observation with a scanning electron microscope.

The sample A was mixed with the untreated red blood cell sample (Sample B) in different ratios between 0% and 80% to provide a series of mixture samples. The mixture samples were visually observed. More specifically, the mixture samples were each stained by the May-Giemsa staining method, and then 1000 red blood cells including normal and fragmented red blood cells were observed on a blood smear film of each of the mixture samples by means of a microscope of a magnification of ×1000 for determination of FRC %. The FROs were herein defined as having a size of 2 $\mu$m to 4 $\mu$m.

Figure 3:
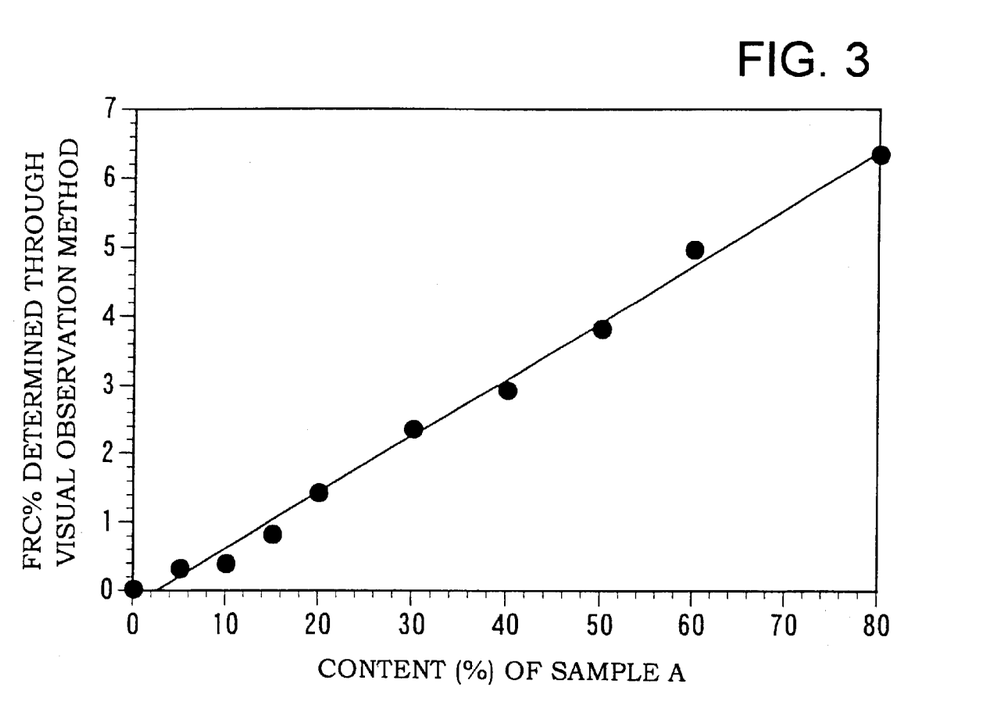
FIG. 3 is a graph showing a relationship between the proportion (%) of a sample A and an FRC % determined through a visual observation method in the embodiment.

The FRC percentages of the series of the mixture samples determined through the visual observation method were in the range between 0% and 7% and, as shown in FIG. 3, have a significant correlation with the content (%) of the sample A. It was confirmed that the series of mixture samples were model samples suitable for development of the inventive analysis method.

Figure 2:
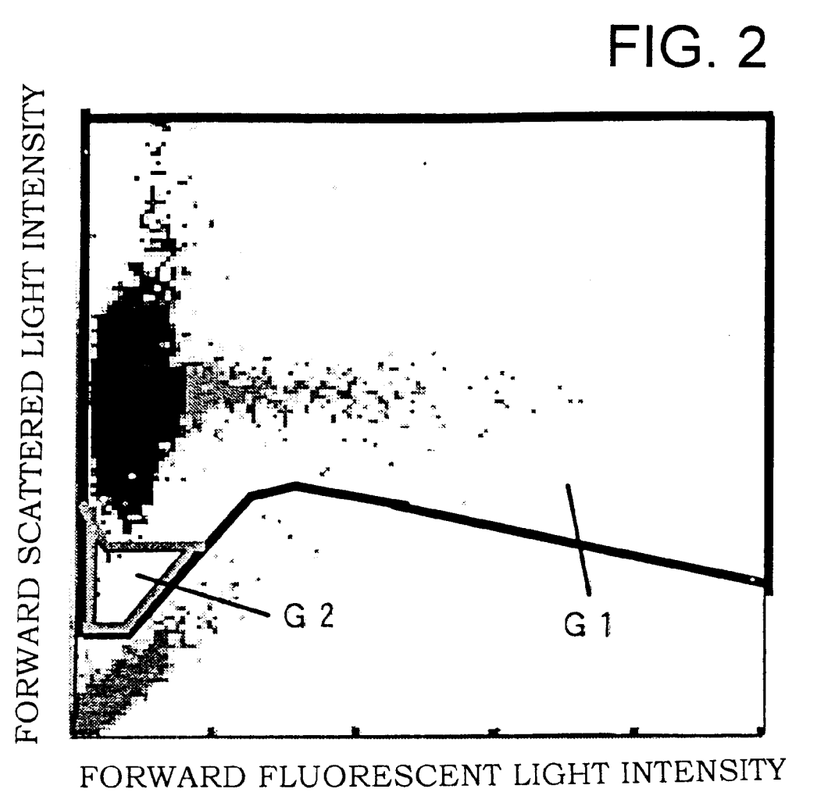
FIG. 2 is a diagram for explaining a two-dimensional scattergram obtained in the embodiment and gates G1 and G2.

Subsequently, the series of mixture samples were analyzed by the analyzer shown in FIG. 1, and a two-dimensional distribution diagram (scattergram) as shown in FIG. 2 was obtained, in which the forward fluorescent light intensity and the forward scattered light intensity were plotted as abscissa and ordinate, respectively. The forward scattered light intensity increases, as the size of a blood cell increases. The forward fluorescent light intensity increases, as the nucleic acid content of the blood cell increases.

In FIG. 2, a gate (area) G1 is a red blood cell (reticulocyte and mature erythrocyte) distribution area defined by a program preliminarily installed in the analyzer (FIG. 1). An area below the gate G1 is a platelet distribution area.

The results of the analysis of the series of mixture samples indicated that the number of dots (particles) falling within a region located on the upper left side of the platelet distribution area (i.e., a region in which the cell size is smaller and the nucleic acid content is lower within the gate G1) tends to increase as the proportion (%) of the sample A increases. Therefore, a gate G2 was properly established in this region as shown in FIG. 2, and the percentage of the dots (particles) falling within the gate G2 was determined by the analyzer.

Figure 4:
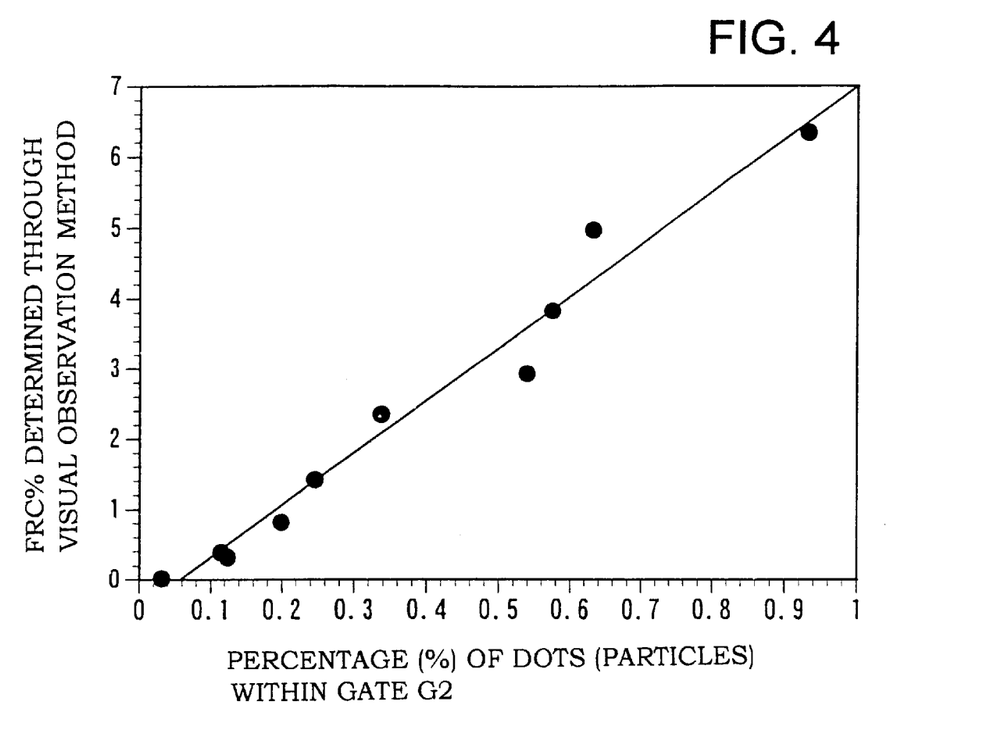
FIG. 4 is a graph showing a relationship between the percentage (%) of dots (particles) falling within the gate G2 and the FRC % determined through the visual observation method in the embodiment.
Figure 5:
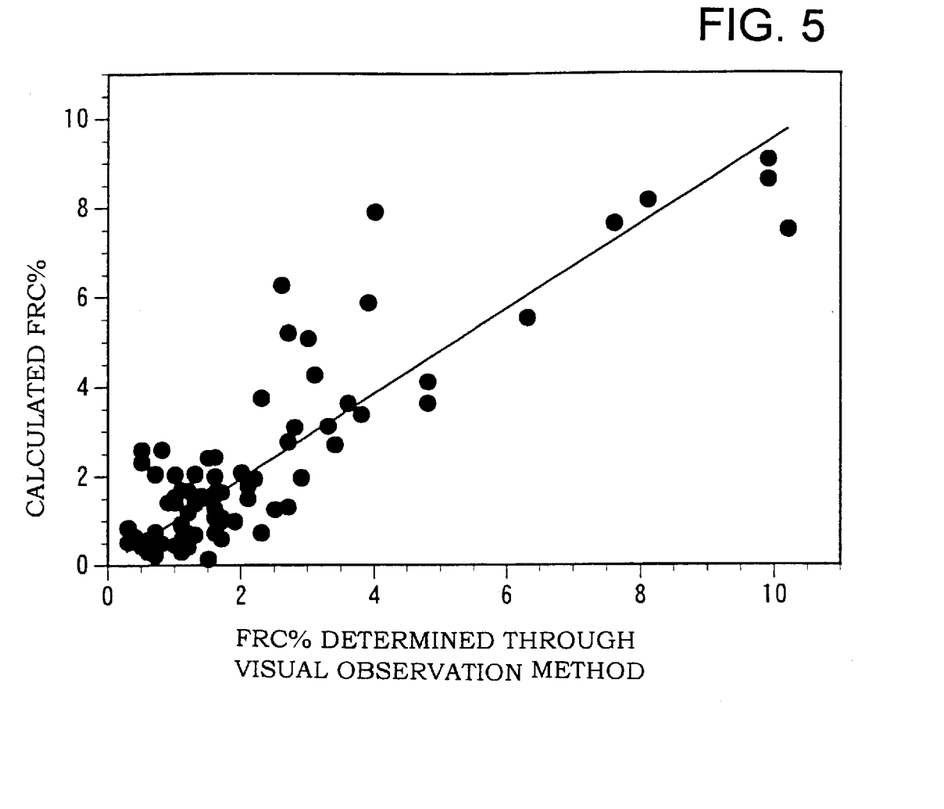
FIG. 5 is a graph showing a relationship between the FRC % determined through the visual observation method and the FRC % calculated in the embodiment.

As a result, it was found that there was a significant correlation between the number of the dots (particles) falling within the gate G2 and the FRC % determined through the visual observation method as shown in FIG. 4.

$$y=7.41x-0.44 \quad (1)$$

wherein y is the FRC % determined through the visual observation method, and x is the percentage of the dots (particles) within the gate G2, i.e., gate G2/gate G1.

(2) Determination of FRC % of Actual Blood Samples

With 90 blood samples each having a normal MCV (mean cell volume) and/or a normal MCHC (mean cell hemoglobin concentration) and containing fragmented red blood cells, FRC percentages were calculated on the basis of the equation (1). There was an advantageous correlation between the FRC % determined through the calculation and the FRC % determined through the visual observation method with no significant difference therebetween (paired t-test, P=0.77).

(3) Correction of FRC %

When the analysis was performed on 17 microcytic hypochromatic blood samples obtained from asiderotic anemia patients and the like, it was found that red blood cells in these samples were plotted at lower positions than those in a normal sample on the scattergram (FIG. 2) on which the FRC detection gate G2 was established. As a result, the number of dots (particles) falling within the gate G2 was significantly increased, so that an apparently higher FRC % was calculated from the equation (1).

Figure 6:
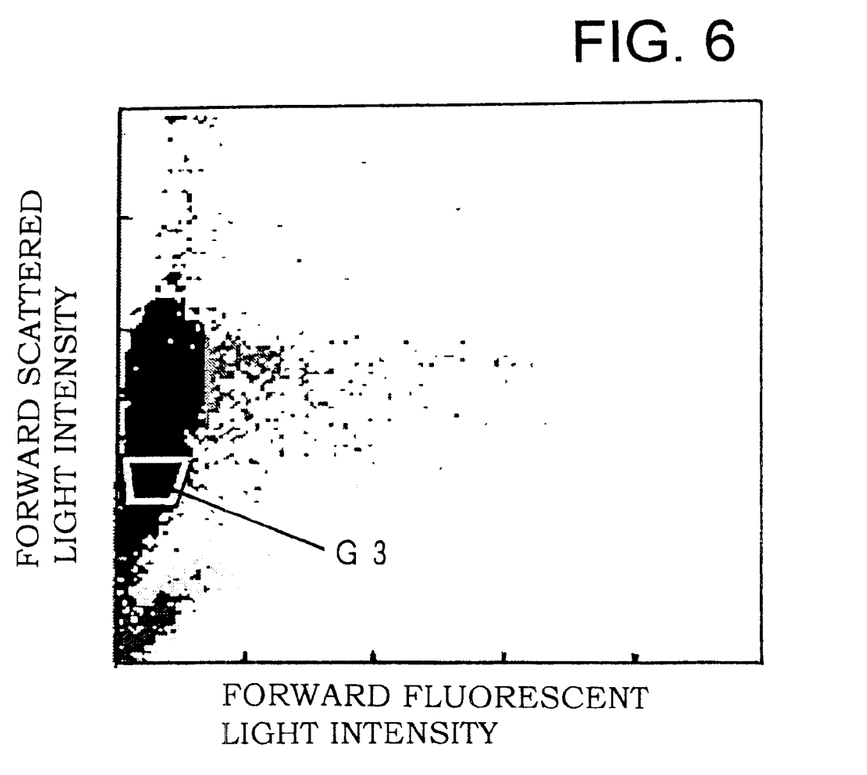
FIG. 6 is a diagram for explaining a two-dimensional scattergram and a gate G3 in accordance with the embodiment.
Figure 7:
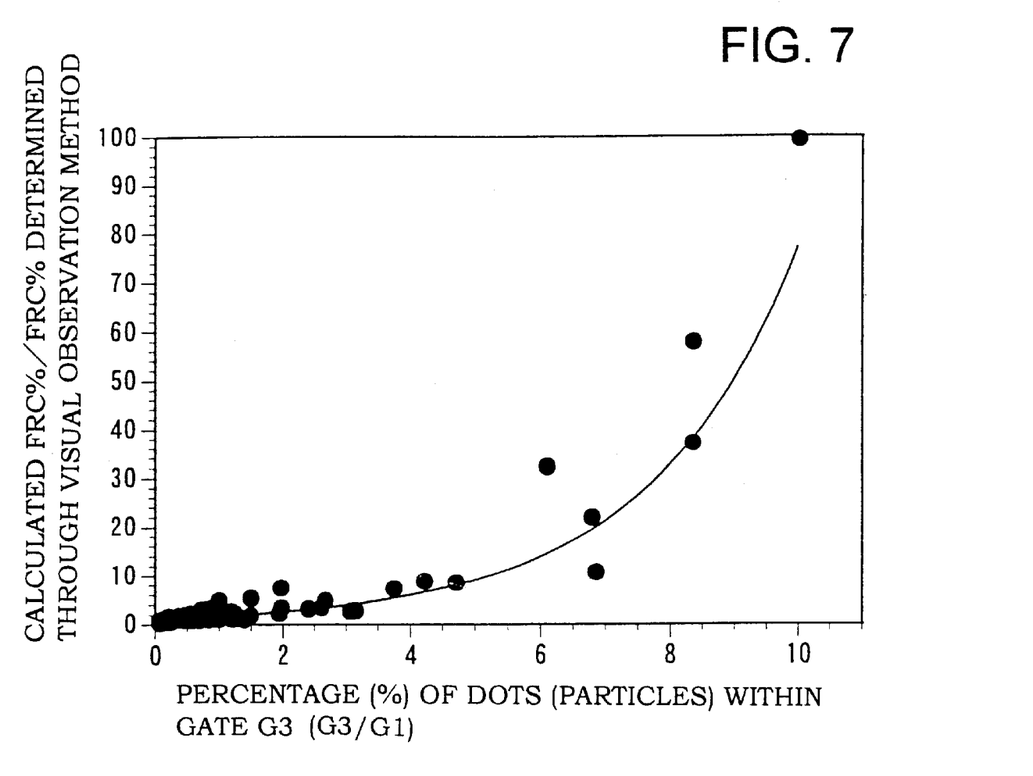
FIG. 7 is a graph showing a relationship between the percentage (G3/G1) of dots (particles) falling within the gate G3 and the ratio of a calculated FRC % to a FRC % determined through the visual observation method.

Therefore, a special gate G3 was established as shown in FIG. 6 to identify this type of samples for correction of the calculated FRC %. The deviation of the calculated FRC % from the true value (which herein means the FRC % determined through the visual observation method) increases (or the ratio of the calculated FRC % to the true FRC % increases), as the number of dots falling within the gate G3 increases. Therefore, the following equation was derived from FIG. 7.

$$y=\exp(0.43x) \quad (2)$$

wherein y is the ratio of the FRC % calculated from the equation (1) to the FRC % determined through the visual observation method, and x is the percentage of the dots (particles) falling within the gate G3, i.e., Gate G3/Gate G1 (%).

As is apparent from FIG. 7, the correction of the calculated FRC % is required when the percentage of the dots (particles) falling within the gate G3 (Gate G3/Gate G1) exceeds a value of 1 to 3 (e.g., 1.5%).

The true FRC % can be calculated from the following equation (3) which is derived from the equation (2):

$$FRC\ \%=(FRC\ \%\ \text{calculated from the equation (1)})/\exp(0.43 \times \text{Gate G3/Gate G1}) \quad (3)$$

Figure 8:
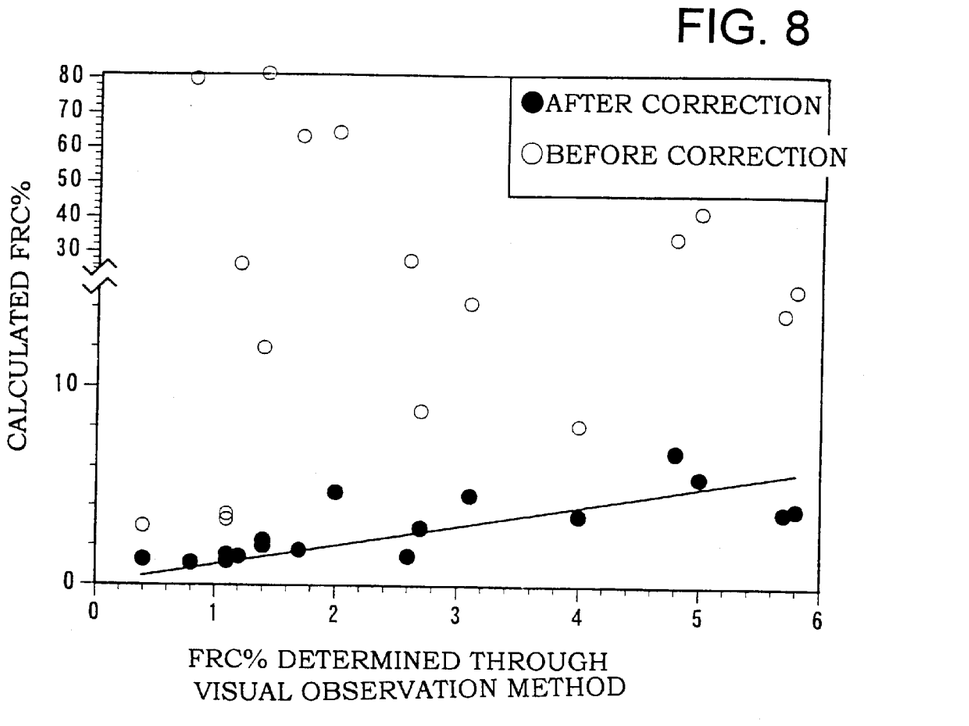
FIG. 8 is a graph showing a relationship between an FRC % determined through the visual observation method and a calculated FRC % for 17 microcytic hypochromatic samples in the embodiment.

With the aforesaid 17 samples, it was confirmed that there was a significant correlation between the corrected FRC % and the FRC % determined through the visual observation method as shown in FIG. 8 with no significant difference therebetween (paired t-test, P=0.43).

(4) Average FRC % of Normal Blood Samples from Healthy Subjects

With 189 normal samples from healthy subjects, the FRC percentages were calculated from the equation (1). The FRC percentages were not higher than 1% (0.14±0.17%). This indicates that there is an extremely low risk that the FRC % gives a decisively erroneous diagnosis.

(5) FRC % of HUS (Hemolytic Uremic Syndrome) Patient Under Treatment

The FRC % of a HUS patient under treatment was monitored through the inventive analysis method. The quantitative analysis indicated that the FRC % decreased from 8.6% to 3.6% in 12 days during which the patient took a clinical treatment with antibiotics and peritoneal dialysis.

The analysis of the fragmented red blood cells (FRCs) is conventionally achieved by the observation of a blood smear film. This method suffers from a lower reproducibility because only 1000 red blood cells are generally counted. On the other hand, the method utilizing the flow cytometer ensures a higher reproducibility because 30000 blood cells are counted on average. Therefore, the inventive method allows for accurate and efficient determination of the FRC % of a subject with a higher reproducibility, and is useful for diagnosis of the diseases.

What is claimed is:

1. A method for quantitatively analyzing fragmented red blood cells, comprising the steps of:

adding a nucleic acid staining fluorochrome dye to a blood sample for preparation of a specimen containing particles;

allowing the specimen to flow through a flow cytometer, and measuring a scattered light intensity and a fluorescent light intensity for each particle in the specimen;

preparing a two-dimensional particle distribution diagram on the basis of the measured scattered light intensity and fluorescent light intensity;

establishing a red blood cell distribution area on the two-dimensional distribution diagram, and counting particles falling within the red blood cell distribution area for determination of the total number A of red blood cells;

establishing a fragmented red blood cell distribution area in the red blood cell distribution area, and counting particles falling within the fragmented red blood cell distribution area for determination of the number B of fragmented red blood cells; and calculating a value B/A, and calculating a content by percentage F of the fragmented red blood cells from a conversion function F=f (B/A).

2. A method for quantitatively analyzing fragmented red blood cells, comprising the steps of:

adding a nucleic acid staining fluorochrome dye to a blood sample for preparation of a specimen containing particles;

allowing the specimen to flow through a flow cytometer, and measuring a scattered light intensity and a fluorescent light intensity for each particle in the specimen;

preparing a two-dimensional particle distribution diagram on the basis of the measured scattered light intensity and fluorescent light intensity;

establishing a red blood cell distribution area on the two-dimensional distribution diagram, and counting particles falling within the red blood cell distribution area for determination of the total number A of red blood cells;

establishing a fragmented red blood cell distribution area in the red blood cell distribution area, and counting particles falling within the fragmented red blood cell distribution area for determination of the number B of fragmented red blood cells;

calculating a value B/A, and calculating a content by percentage F of the fragmented red blood cells from a conversion function F=f(B/A);

establishing a microerythrocyte distribution area in a region in which the scattered light intensity is higher than in the fragmented red blood cell distribution area within the red blood cell distribution area;

counting particles falling within this area for determination of the number C of microerythrocytes; and correcting the content by percentage F on the basis of C/A.

3. The method of claim 2, wherein in the step of calculating the fragmented red blood cell percentage F, the value F is corrected on the basis of the value C/A when the value C/A is greater than a predetermined value $\alpha$.

4. The method of claim 3, wherein the value F is calculated from the function F=f(B/A) when the value of C/A is not greater than a predetermined value $\alpha$, and calculated on the basis of a function $F=f(B/A)\cdot\exp\{-a(C/A)\}$, wherein "a" is a constant and when the value C/A is greater than the predetermined value.

5. The method of claim 4, wherein the constant a is 0.43.

6. The method of claim 3, wherein the predetermined value $\alpha$ is between 1 and 3 percent.

7. A method for quantitatively analyzing fragmented red blood cells, comprising the steps of:

adding a nucleic acid staining fluorochrome dye to a blood sample for preparation of a specimen containing particles;

allowing the specimen to flow through a flow cytometer, and measuring a scattered light intensity and a fluorescent light intensity for each particle in the specimen;

preparing a two-dimensional particle distribution diagram on the basis of the measured scattered light intensity and fluorescent light intensity;

establishing a red blood cell distribution area on the two-dimensional distribution diagram, and counting particles falling within the red blood cell distribution area for determination of the total number A of red blood cells;

establishing a fragmented red blood cell distribution area in the red blood cell distribution area, and counting particles falling within the fragmented red blood cell distribution area for determination of the number B of fragmented red blood cells; and calculating a value B/A, and calculating a content by percentage F of the fragmented red blood cells from a conversion function F=f(B/A), wherein the conversion function F=f(B/A) is expressed as a linear equation F=m(B/A)+n wherein "m" and "n" are constants.

8. An apparatus for analyzing fragmented red blood cells, comprising:

a flow cell for flowing a specimen containing particles therein, the specimen being prepared by adding a nucleic acid staining fluorochrome dye to a blood sample;

a light source for emitting a light beam to the particles in the specimen;

a first detector for detecting an intensity of scattered light generated from each particle;

a second detector for detecting an intensity of fluorescent light generated from each particle; and a data processor for processing the detected intensities, wherein the data processor carries out, a first step of preparing a two-dimensional particle distribution diagram on the basis of the measured scattered light intensity and fluorescent light intensity;

a second step of establishing a red blood cell distribution area on the two-dimensional diagram, and counting particles falling within the red blood cell distribution area for determination of the total number A of red blood cells;

a third step of establishing a fragmented red blood cell distribution area in the red blood cell distribution area, and counting particles falling within the fragmented red blood cell distribution area for determination of the number B of fragmented red blood cells; and a fourth step of calculating a value B/A, and calculating a content by percentage F of the fragmented red blood cells from a conversion function F=f(B/A).

* * * * *